US011033681B2

(12) United States Patent
Eitan et al.

(10) Patent No.: US 11,033,681 B2
(45) Date of Patent: Jun. 15, 2021

(54) AUTOMATIC CATHETER RECOGNITION AND ASSOCIATED METHODS, SYSTEMS AND CIRCUITS

(71) Applicant: Q-CORE MEDICAL LTD., Netanya (IL)

(72) Inventors: Boaz Eitan, Hofit (IL); Nimrod Schweitzer, Tel Aviv (IL); Dafna Kesselman, Tel Aviv (IL); Nora Lisman, Netanya (IL); Andrei Yosef, Even Yehuda (IL)

(73) Assignee: Q-CORE MEDICAL LTD., Netanya (IL)

( * ) Notice: Subject to any disclaimer, the term of this patent is extended or adjusted under 35 U.S.C. 154(b) by 147 days.

(21) Appl. No.: 15/990,658

(22) Filed: May 27, 2018

(65) Prior Publication Data
US 2018/0318505 A1    Nov. 8, 2018

Related U.S. Application Data

(63) Continuation of application No. 14/830,772, filed on Aug. 20, 2015, now abandoned.

(51) Int. Cl.
*A61M 5/168*    (2006.01)
*A61M 5/142*    (2006.01)

(52) U.S. Cl.
CPC ........ *A61M 5/16854* (2013.01); *A61M 5/142* (2013.01); *A61M 5/16877* (2013.01); *A61M 2005/16868* (2013.01); *A61M 2205/14* (2013.01); *A61M 2205/18* (2013.01); *A61M 2205/3368* (2013.01); *A61M 2205/505* (2013.01)

(58) Field of Classification Search
CPC .............. A61M 5/16854; A61M 5/142; A61M 5/16877
See application file for complete search history.

(56) References Cited

U.S. PATENT DOCUMENTS

| 5,096,385 A | 3/1992 | Georgi et al. |
| 5,843,035 A | 12/1998 | Bowman et al. |
| 8,142,400 B2 | 3/2012 | Rotem et al. |
| 2003/0141468 A1 | 7/2003 | Malmstrom et al. |
| 2005/0107923 A1 | 5/2005 | Vanderveen |

(Continued)

FOREIGN PATENT DOCUMENTS

| CN | 103727021 A | 4/2014 |
| NO | 2017/184777 A1 | 10/2017 |

(Continued)

OTHER PUBLICATIONS

Extended European Search Report which issued in EP20160966.6.

(Continued)

*Primary Examiner* — Bradley J Osinski
(74) *Attorney, Agent, or Firm* — The Roy Gross Law Firm, LLC; Roy Gross

(57) ABSTRACT

Disclosed is a medical device for pumping fluid through a conduit, the pump including: one or more sensors to detect a parameter associated with the fluid; a circuit to (a) receive from the sensor a first signal indicative of one or more characteristics associated with the fluid; and (b) to determine if an occlusion is indicated based on a signal analysis of the first signal.

10 Claims, 13 Drawing Sheets

(56) References Cited

U.S. PATENT DOCUMENTS

| | | |
|---|---|---|
| 2006/0173421 A1 | 8/2006 | Weber et al. |
| 2006/0189926 A1 | 8/2006 | Hall et al. |
| 2006/0206054 A1 | 9/2006 | Shekalim |
| 2007/0123781 A1 | 5/2007 | Callahan et al. |
| 2007/0179435 A1 | 8/2007 | Braig et al. |
| 2008/0283296 A1 | 11/2008 | Zamora et al. |
| 2009/0293588 A1 | 12/2009 | Riley et al. |
| 2010/0114001 A1 | 5/2010 | O'Mahony |
| 2010/0212407 A1 | 8/2010 | Stringham et al. |
| 2010/0280446 A1* | 11/2010 | Kalpin ............... A61M 5/14276 604/67 |
| 2011/0190606 A1 | 8/2011 | Gable et al. |
| 2012/0205312 A1 | 8/2012 | Hogard |
| 2012/0238949 A1 | 9/2012 | Kaplin |
| 2012/0330574 A1 | 12/2012 | Ruiter et al. |
| 2013/0336814 A1 | 12/2013 | Kamen et al. |
| 2014/0119954 A1 | 5/2014 | Schweitzer et al. |
| 2014/0228755 A1 | 8/2014 | Darrah et al. |
| 2015/0005699 A1 | 1/2015 | Burbank et al. |
| 2015/0367120 A1 | 12/2015 | Kusters et al. |

FOREIGN PATENT DOCUMENTS

| | | |
|---|---|---|
| WO | 2009/042061 A2 | 4/2009 |
| WO | 2009/047721 | 4/2009 |
| WO | 2012151077 | 11/2012 |

OTHER PUBLICATIONS

Office Action dated Jun. 22, 2020 which issued in U.S. Appl. No. 15/740,365.

An Office Action together with an English summary dated Jun. 23, 2020, which issued during the prosecution of Chinese Patent Application No. 201690050050.8.

European Search Report for Patent Application No. EP20208122, dated Apr. 22, 2021, 9 pages.

\* cited by examiner

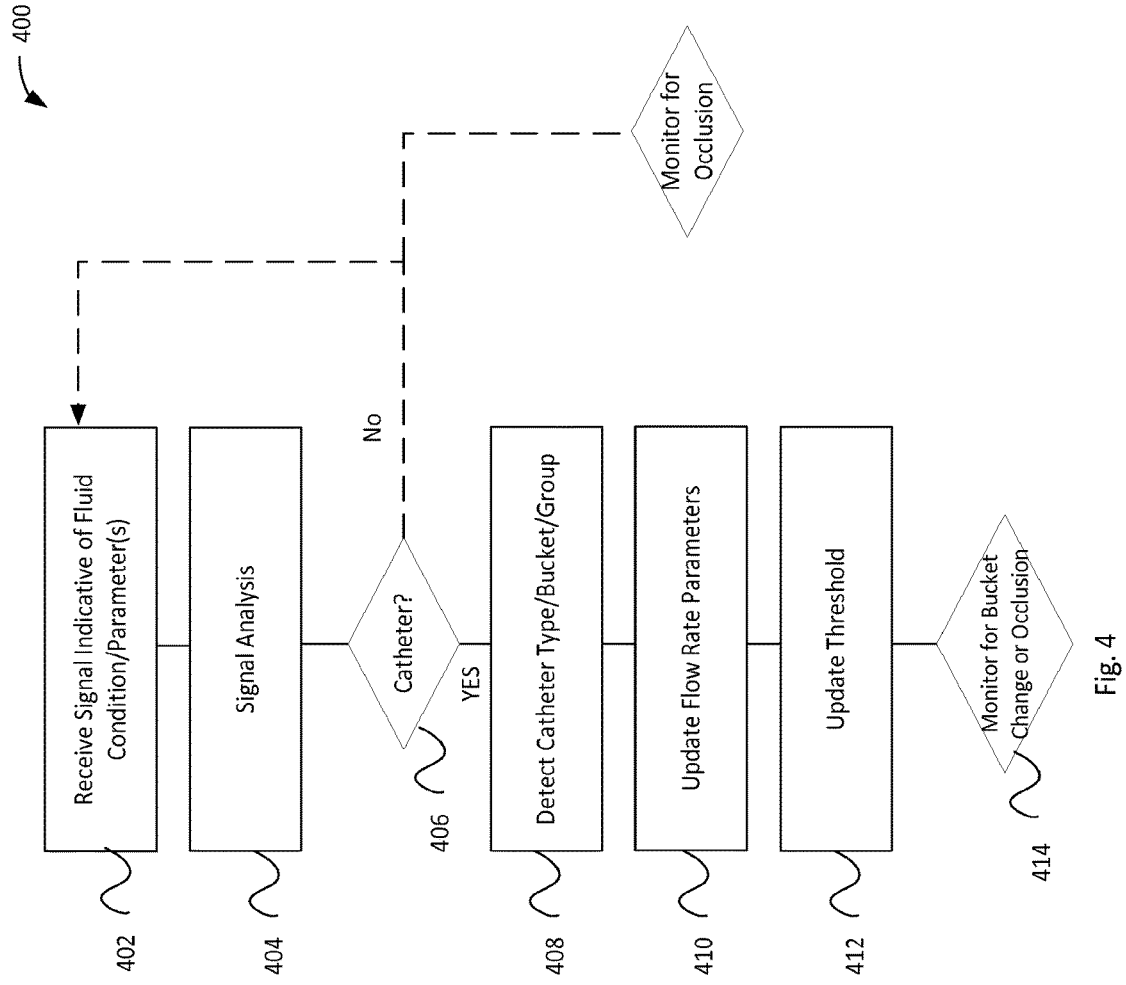

| Modes | Conditions for occlusion | Is prompted at | Result |
|---|---|---|---|
| All modes | a. 4 consecutive $Min$ reductions<br>b. Sum of $Min$ deltas > 50 A/D<br>c. $\Delta(Fout-Min)$ > 50 A/D | When detected | Upstream occlusion |
| | a. 4 consecutive $Fout$ increases<br>b. Sum of $Fout$ deltas > 50 A/D<br>c. $\Delta(Fout-Min)$ > 115 A/D | After bucket is set, not before $8^{th}$ cycle | Downstream occlusion |
| | a. 4 consecutive $Min$ reductions<br>b. Sum of $Min$ deltas > 115 A/D | When detected | Upstream occlusion |
| | a. 4 consecutive $Fout$ increases<br>b. Sum of $Fout$ deltas > 115 A/D | After bucket is set, not before $8^{th}$ cycle | Downstream occlusion |
| | $\Delta(Fout-Min)$ > 115 A/D | After bucket is set, not before $8^{th}$ cycle | Occlusion |
| | a. $Min$ < 300A/D<br>b. $\Delta(Fout-Min)$ > 50 A/D | When detected | Upstream occlusion |

Fig. 6C

| Measured $\Delta(Fout-Min)$ | Bucket # |
|---|---|
| 0-40 | 0 |
| 40-60 | 1 |
| 60-80 | 2 |
| 80-100 | 3 |
| 100-115 | 4 |

Fig. 6D

| Bucket # | $\Delta(Fout-Min)$ to trigger transition to next bucket | Conversion factor per bucket | $\Delta(Fout-Min)$ to trigger transition to previous bucket (hysteresis) |
|---|---|---|---|
| 0 | 40 | 0% | -- |
| 1 | 60 | -5% | 30 |
| 2 | 80 | -10% | 50 |
| 3 | 100 | -20% | 70 |
| 4 | 115 | -30% | 90 |

Fig. 6E

|  | 125 ml/h accuracy | 200 ml/h accuracy | bucket | Conversion factor | Threshold value | Threshold value-Epidural |
|---|---|---|---|---|---|---|
| None | 0.00% | 0.00% | 0 | 0 | 50 | |
| Epidural Type 1 (16G) | -8.99% | -9.13% | | | | 115 |
| PERIFIX 19G | -9.77% | -10.27% | | | | |
| Umbilical | -13.11% | -15.99% | 1 | -10.5% | 90 | |
| Epidural Type 2 (18G) | -14.13% | -18.16% | | | | |
| SPINAL NEEDLE 27G | -14.70% | -19.06% | | | | |
| Pediatric 24G | -24.64% | -30.02% | 2 | -20.0% | 114 | |
| PICC | -29.02% | -35.72% | | | | |

Fig. 7A

| Example flow characteristics | Accuracy without bucket change [% deviation from nominal flow rate] | Bucket type | % change to flow parameters | Accuracy with bucket change [% deviation from nominal flow rate] |
|---|---|---|---|---|
| catheter type 1 | -45% | 5 | none | occlusion |
| catheter type 2 | -35% | 4 | -30% | -10% |
| catheter type 3 | -25% | 3 | -20% | -8% |
| catheter type 4 | -15% | 2 | -10% | -5% |
| catheter type 5 | -3% | 1 | -5% | 1% |
| no catheter | 0.60% | 0 | none | 0.60% |

Fig. 7B

AUTOMATIC CATHETER RECOGNITION AND ASSOCIATED METHODS, SYSTEMS AND CIRCUITS

CROSS REFERENCE TO RELATED APPLICATIONS

This application is a continuation of U.S. application Ser. No. 14/830,772 filed Aug. 20, 2015. The contents of this application is incorporated by reference as if fully set forth herein in its entirety.

FIELD OF THE INVENTION

The present invention relates generally to the field of medical devices. More specifically, the present invention relates to detection of catheters placed in conjunction with a medical device.

BACKGROUND

Medical devices operate for therapeutic and/or diagnostic uses. Some example medical devices may include: peristaltic pumps which may be used to infuse medicines into a patient's body, blood pressure monitors which may monitor a patient's blood pressure and heart rate, electrical thermometers which may measure a patient's body temperature and many more.

A medical device may be used in a hospital, doctor or nurse's office or other medical treatment centers. Medical devices may also be used at patient's homes or personal environments.

Some medical devices may be used to transport/lead fluid to and/or from a patient through a conduit. Some systems may include a medical device, a first conduit and optionally a catheter.

Some medical devices as discussed above may detect an occlusion in the fluid. An occlusion may be caused by a bend in the conduit, a clamp being closed, a flow regulator being closed, an inline blood clot, a medication coagulation or a patient leaning on the conduit or otherwise and more.

Some medical devices include pumps such as peristaltic pumps which may cause fluid to flow through a conduit. The pumps may include camshafts and/or one or more fingers or actuators as part of a pumping mechanism. A pump may also have a pump cycle during which a predetermined amount of fluid is caused to flow through the conduit.

A medical device may include a requested flow rate which may be input by a user or calculated based on other user inputs and/or automatically received based on the selected therapy being provided by the medical device.

SUMMARY OF THE INVENTION

According to some embodiments, a medical device for pumping fluid through a conduit, may include: one or more sensors to detect a parameter associated with the fluid, a circuit to (a) receive from the one or more sensors a first signal indicative of one or more characteristics associated with the fluid; (b) to determine if a conduit pressure passes a first fluid-parameter-threshold based on the first signal; and (c) if the conduit pressure passes the first fluid-parameter-threshold, determine if an occlusion is indicated or a catheter is connected to the conduit.

According to some embodiments, a medical device may further include a feedback circuit to cause a flow rate parameter associated with the medical device to be updated if a catheter is determined to be connected so that a requested flow rate may be achieved. The first fluid parameter may be a backpressure and/or a flow rate. The circuit may be configured to update the first fluid-parameter threshold to a second fluid-parameter threshold if a catheter is determined to be connected to the conduit. The sensor may be a pressure sensor for detecting a pressure of the fluid in the conduit. The medical device may include a pumping mechanism. The circuit may be configured to stop the pumping mechanism for a determined length of time and receive the first signal to determine if a catheter is connected.

According to some embodiments, a method of detecting a catheter downstream to a medical device, may include receiving a signal from a sensor, the signal indicative of a fluid parameter associated with the fluid in the conduit; analyzing the signal to identify an occlusion, a catheter or a non-catheter state; and producing an indicator associated with the occlusion, catheter or non-catheter state.

According to some embodiments, the method may include updating a fluid-parameter threshold based on the indicator if an occlusion was identified. Analyzing may include identifying the catheter group if a catheter is identified.

According to some embodiments, a peristaltic pump for pumping fluid through a conduit may include one or more sensors to detect a parameter associated with the fluid; a circuit to (a) receive from the sensor a first signal indicative of one or more characteristics associated with the fluid; (b) to determine if an occlusion is indicated or a catheter is connected to the conduit based on a signal analysis of the first signal. The signal analysis may include comparing a signal value to two or more predetermined value ranges wherein a first value range indicates an occlusion and a second value range indicates a first catheter bucket. Optionally, a third value range may indicate a second catheter bucket and a fourth value range may indicate either a third catheter bucket or a non-catheter indication. The signal value may be sampled at a determined sampling point. Wherein the sampling point may be a defined number of cycles, a defined number of cam rotations, a defined length of time or otherwise. The sampling point may be selected at least partially according to a selected flow rate.

The present invention includes methods for automatic recognition of a catheter being placed in conjunction with a medical device and associated methods, systems and circuits. According to some embodiments of the present invention, a medical device may be configured to operate in conjunction with a conduit and configured to cause fluid to flow through the conduit. The medical device may be further configured to: (a) receive a signal associated with the flow of fluid through the conduit and based on the signal to detect a catheter; (b) if a catheter is detected a feedback circuit or a controller may cause (i) parameters associated with the flow rate (which may also be termed flow rate parameter(s)) to be updated so that a nominal flow rate taking into account the detected catheter characterization is compensated for; and (ii) a fluid-parameter-threshold to be updated so that unneeded occlusion alarms stemming from the catheter (and not an actual occlusion) are avoided/withheld/deferred and optionally (c) differentiate between a catheter and an occlusion.

According to some embodiments, the medical device may detect a catheter according to a signal received from a sensor of the medical device such that expected parameters associated with the catheter are detected.

According to some embodiments, the medical device may differentiate between an occlusion and a catheter according to a signal received from a sensor of the medical device such that parameters associated with an occlusion are differentiated from parameters associated with a downstream catheter.

According to some embodiments, the medical device may be configured to automatically identify if a catheter is connected to the conduit, typically, downstream from the medical device. A downstream catheter may cause a decrease in the medical device output flow rate. The medical device may be configured to automatically identify if a catheter is connected to the conduit, typically, downstream from the medical device. A downstream catheter may cause a decrease in the medical device output flow rate or may cause an increase in back pressure toward the medical device or otherwise.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4 is a flow chart of an example method in accordance with some embodiments of the present invention;

FIGS. 6C-6E include tables associated with some example methods, in accordance with some embodiments of the present invention; and FIGS. 7A and 7B are charts of an example summary/comparison table in accordance with some embodiments of the present invention showing example values.

Figure 1:
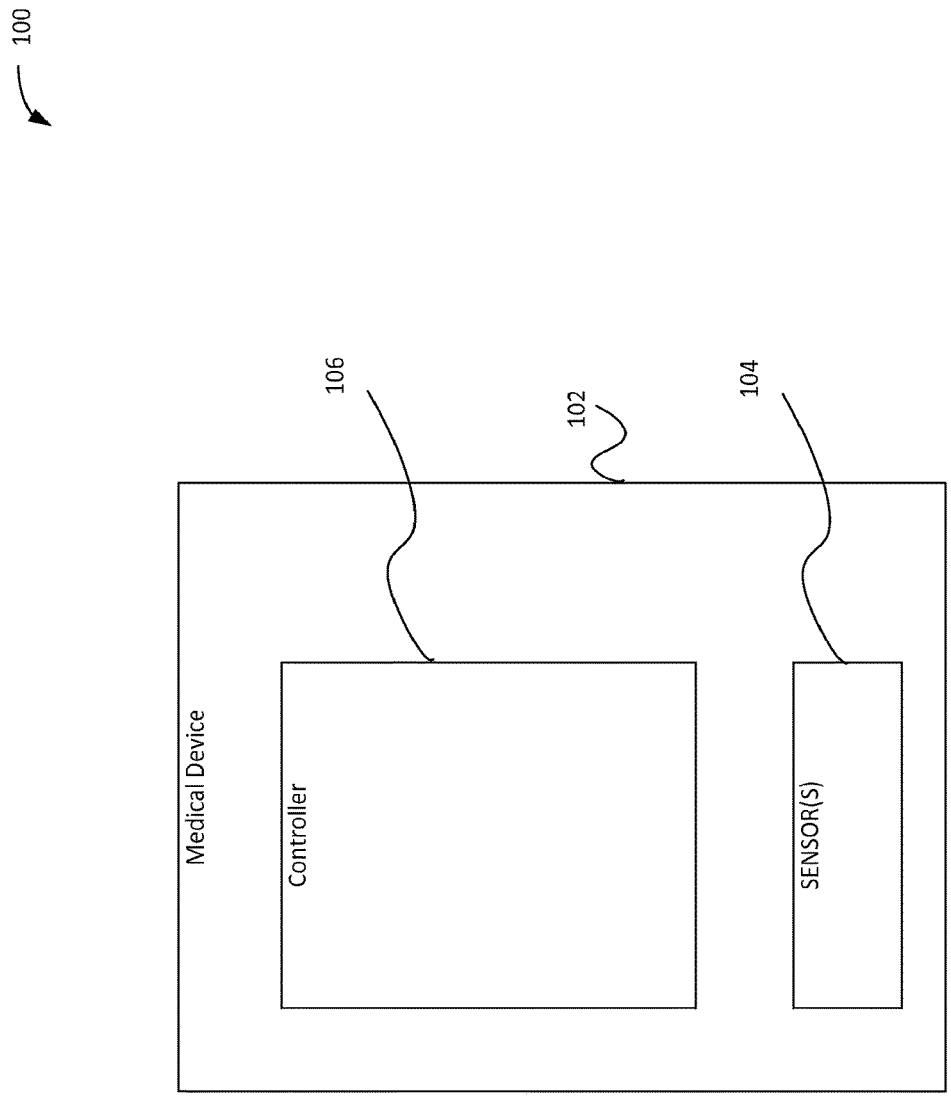
FIG. 1 is a block level diagrams of an example medical device in accordance with some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

Some of the processes and displays presented herein with regarding to the medical device computer/circuit of the medical device are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

According to some embodiments, a medical device may be configured to cause fluid to flow from a fluid source to a downstream direction and may include a pumping mechanism. The medical device may operate in conjunction with a first conduit. Optionally, a second conduit, such as a catheter, may be connected to the first conduit downstream from the medical device. Typically, it may be unknown at/to the medical device if a catheter is present/connected downstream or not and/or the type of catheter being used and its physical parameters/characterization (width, length etc.). It is customary in the field that catheters may also be placed in conjunction to a patient or in a patient's body. Possibly, the presence or non-presence of a downstream catheter may not be known to the health provider connecting the patient to a medical device, or the type/size/characterization of the catheter may not be known. Regardless, typically, the health provider or clinician may not know how a catheter affects the backpressure or flow rate of a medical device.

According to some embodiments, the second conduit/catheter may optionally have a narrower cross section/width than the first conduit which may cause backpressure in the direction of the medical device (or a decrease in the medical device output pressure). An elevated backpressure may cause the medical device to inaccurately detect an occlusion and in some configurations may cause the flow rate to be different than the requested flow rate. It is noted that while a second conduit and a catheter are discussed above, for clarity of the following description a catheter will be discussed while the meaning should be interpreted to include any conduit functioning as described with regard to the catheter. Furthermore, while detection of a catheter is discussed it is understood that a catheter having a width which does not cause an increase in backpressure or the like may not be detected as it may not affect operation of the medical device. Similarly, a catheter may be considered an occlusion if it causes higher backpressure than the maximal catheter group and/or a higher backpressure than can be substantially compensated for.

The present invention includes methods for automatic recognition of a catheter being placed in conjunction with a medical device and associated methods, systems and circuits. According to some embodiments of the present invention, a medical device may be configured to operate in conjunction with a conduit and configured to cause fluid to flow through the conduit. The medical device may be further configured to (a) receive a signal associated with the flow of fluid through the conduit and based on the signal to detect a catheter; (b) if a catheter is detected a feedback circuit or a controller may cause (i) parameters associated with the flow rate (which may also be termed flow rate parameter(s)) to be updated so that a nominal flow rate taking into account the detected catheter characterization is compensated for; and (ii) a fluid-parameter-threshold to be updated so that unneeded occlusion alarms stemming from the catheter (and not an actual occlusion) are avoided/withheld/deferred and optionally (c) differentiate between a catheter and an occlusion.

According to some embodiments, the medical device may detect a catheter according to a signal received from a sensor of the medical device such that expected parameters associated with the catheter are detected.

According to some embodiments, the medical device may differentiate between an occlusion and a downstream catheter according to a signal received from a sensor such that parameters, signal values and/or signal behavior associated with an occlusion are differentiated from parameters, signal values and/or signal behavior associated with a downstream catheter.

According to some embodiments, the medical device may be configured to automatically identify if a catheter is connected to the conduit, typically, downstream from the medical device. A downstream catheter may cause a decrease in the medical device output flow rate and/or may cause an increase in back pressure and/or otherwise.

Turning to FIG. 1, depicted is a block level diagram (100) of an example medical device in accordance with some embodiments. Medical device 102 may be a peristaltic pump, infusion pump, syringe pump, enteral pump, dialysis machine, heart and lung machine or a combination of the above or any medical device configured to cause fluid to flow from a fluid source to a destination and accordingly may include a pumping mechanism. An example destination may include a patient downstream from the medical device.

According to some embodiments, medical device 102 may operate in conjunction with a conduit to cause fluid to flow from a fluid source to a patient or to a downstream destination. The fluid may be saline, water, Total Parenteral Nutrition (TPN), lipids, IV medication, epidural medication, blood and blood products or a combination of any of these and more.

According to some embodiments medical device 102 may include one or more sensors such as sensor 104 which may be configured to detect at least one parameter of the fluid. Sensor 104 may be configured to detect a signal associated with: fluid flow rate, occlusion of fluid, air bubble detection, fluid/conduit pressure and to output a signal to indicate the detected fluid/conduit parameter/characteristic.

According to some embodiments, sensor 104 may be a pressure sensor, a flow rate sensor, a flow meter, a force sensor, a temperature sensor, an infra-red (IR) sensor, Piezo Electric sensor and/or strain gauge or otherwise and/or a combination of these and more.

According to some embodiments, the sensor's output may be an analog or digital signal, the signal may be in the time, frequency, period domain or otherwise.

Medical device 102 may also include a controller such as controller 106. Controller 106 may be one or more circuits some of which may be logical circuits, a microcontroller, and/or module and may include software elements.

According to some embodiments, controller 106 may be configured to control therapeutic functionality of the medical device such as controlling electro-mechanical functionalities of the medical device such as including causing fluid to flow, starting and stopping treatment/therapeutic functionality of the medical device, triggering alarms and more.

According to some embodiments, controller 106 may be configured to receive one or more signals from sensor 104. The signal received from sensor 104 may be an output of sensor 104 and may be indicative of one or more characteristics associated with the fluid. Controller 106 may be configured to conduct a signal analysis of one or more signals received from sensor 104 to detect a catheter type/group and/or differentiate between a catheter and an occlusion.

Figure 2:
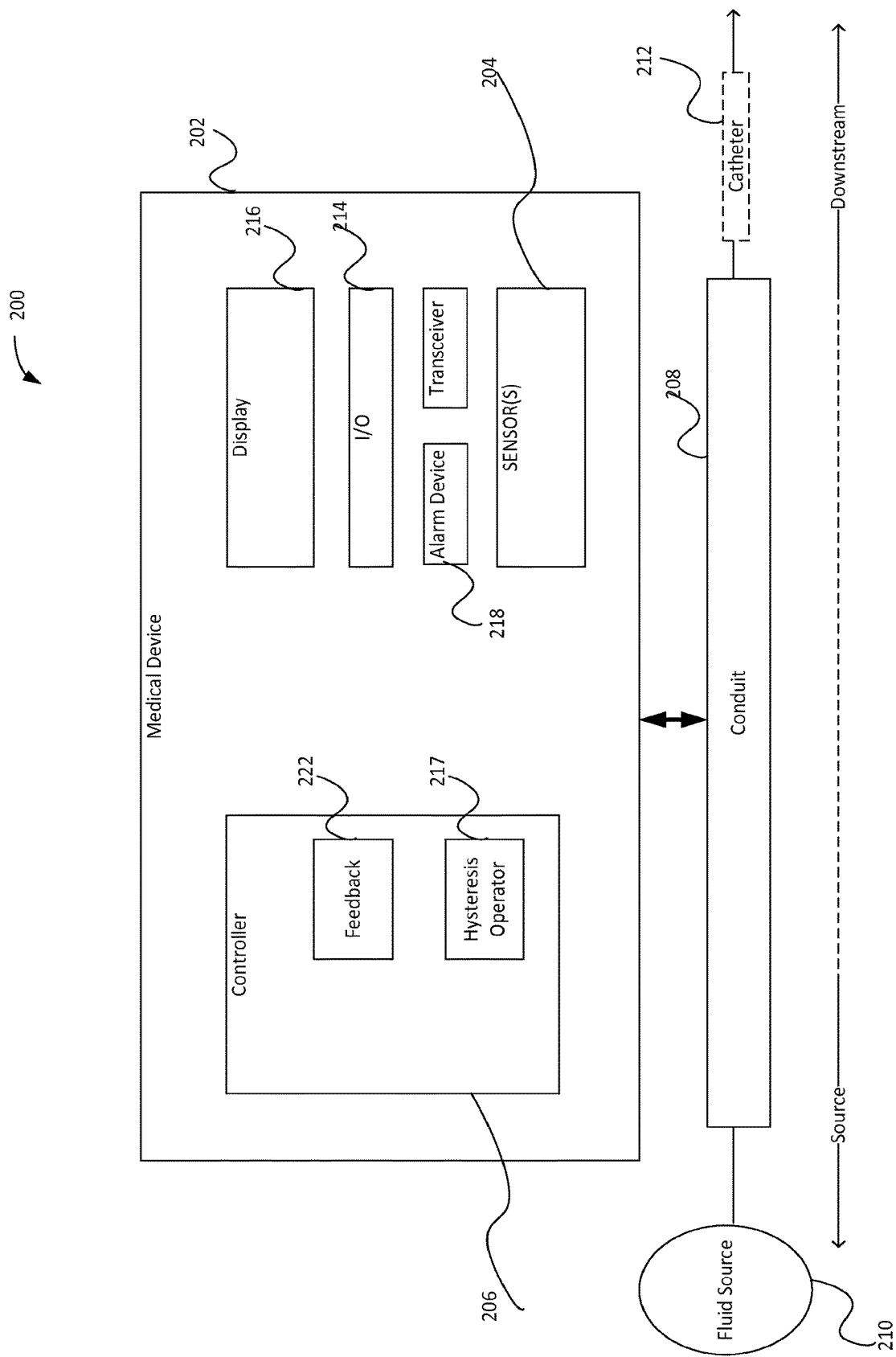
FIG. 2 is a block level diagram of an example system including an example medical device, all in accordance with some embodiments of the present invention.

Turning to FIG. 2, shown is a block level diagram of an example system 200 including an example medical device 202. It is understood that elements 202, 204 and 206 are substantially similar to elements 102, 104 and 106 of FIG. 1. According to some embodiments, medical device 202 may be a pump such a peristaltic pump, syringe pump, enteral pump, vet pump or otherwise, and may cause fluid to flow through conduit 208, which may be placed in conjunction with medical device 202. Conduit 208 may receive fluid from fluid source 210, which may also be in an upstream location to medical device 202. Medical device 202 may cause fluid to substantially flow from fluid source 210 in a downstream direction to a destination such as a patient, a subsequent medical device or otherwise. Optionally, a catheter may be placed downstream from the conduit such as catheter 212. Catheter 212 is depicted in dashed lines to indicate that existence of the catheter is optional and it may be unknown if the catheter is placed or not. Accordingly, existence of catheter 212 may be detected (if it is indeed present) and/or the effect of the catheter 212 on the medical device may be unknown and detected and/or compensated for all as will be discussed in the following embodiments. Controller 206 may receive a signal associated with a pressure of fluid flowing through conduit 208 from sensor 204.

According to some embodiments, controller 206 may be configured to receive one or more signals from sensor 204, which may be indicative of one or more characteristics associated with the fluid. Controller 206 may be configured to conduct a signal analysis of one or more signals received from sensor 204 to detect a catheter and/or differentiate between a catheter and an occlusion and/or detect the catheter type/group/bucket.

Figure 3A:
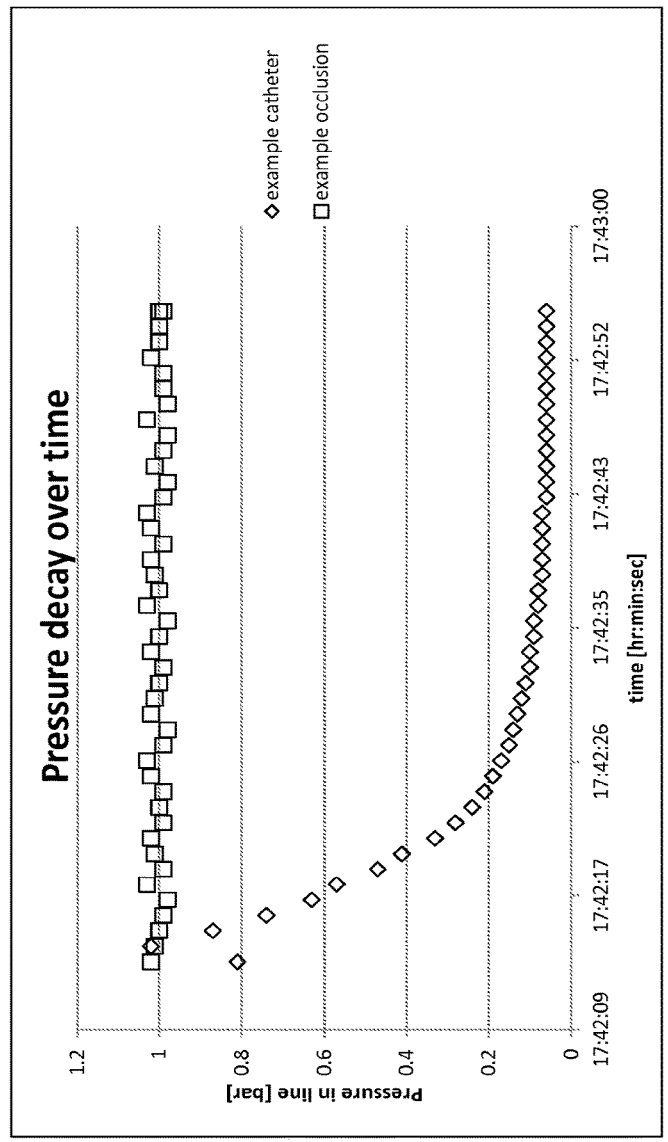
FIGS. 3A-3C are graphs depicting example sensor output results in accordance with some embodiments of the present invention.

Some example groups of embodiments describing the signal analysis will now be discussed. According to a first group of embodiments, controller 206 may detect a fluid parameter is above/has passed a first fluid-parameter threshold. If the first fluid-parameter threshold is passed or exceeded, controller 206 may cause medical device 202 to stop a therapeutic action/functionality of medical device 202 (such as pumping). Optionally, after a predetermined stall/waiting period controller 206 may analyze the signal from sensor 204 to detect if (a) the fluid parameter has passed back over or decayed below a defined value and/or percentage of the initial/prior fluid parameter, in which case a catheter may be indicated or (b) the fluid parameter is above a second fluid-parameter threshold in which case an occlusion may be indicated. Optionally, the fluid parameter may be fluid pressure and the fluid-parameter threshold may be a pressure threshold. Turning to FIG. 3A, depicted is graph 300A showing an example input from sensor 206 following a cessation of the pumping action of medical device 202 after a first fluid-parameter threshold was exceeded if an occlusion is indicated (square dashed line) or if catheter 212 is detected (diamond dashed bottom line), it is clear that in this example the decline of pressure if a catheter is existent downstream is different than the substantially constant/fixed pressure output if an occlusion exists. In this example, the microcontroller may analyze the sensor signal at a sampling point for example at approximately 10 seconds after stopping pumping but anytime between 1 s-30 s may be applicable. Different times, results and graphs may vary depending on flow rate, medical device, conduit and/or catheter parameters and more.

Figure 3B:
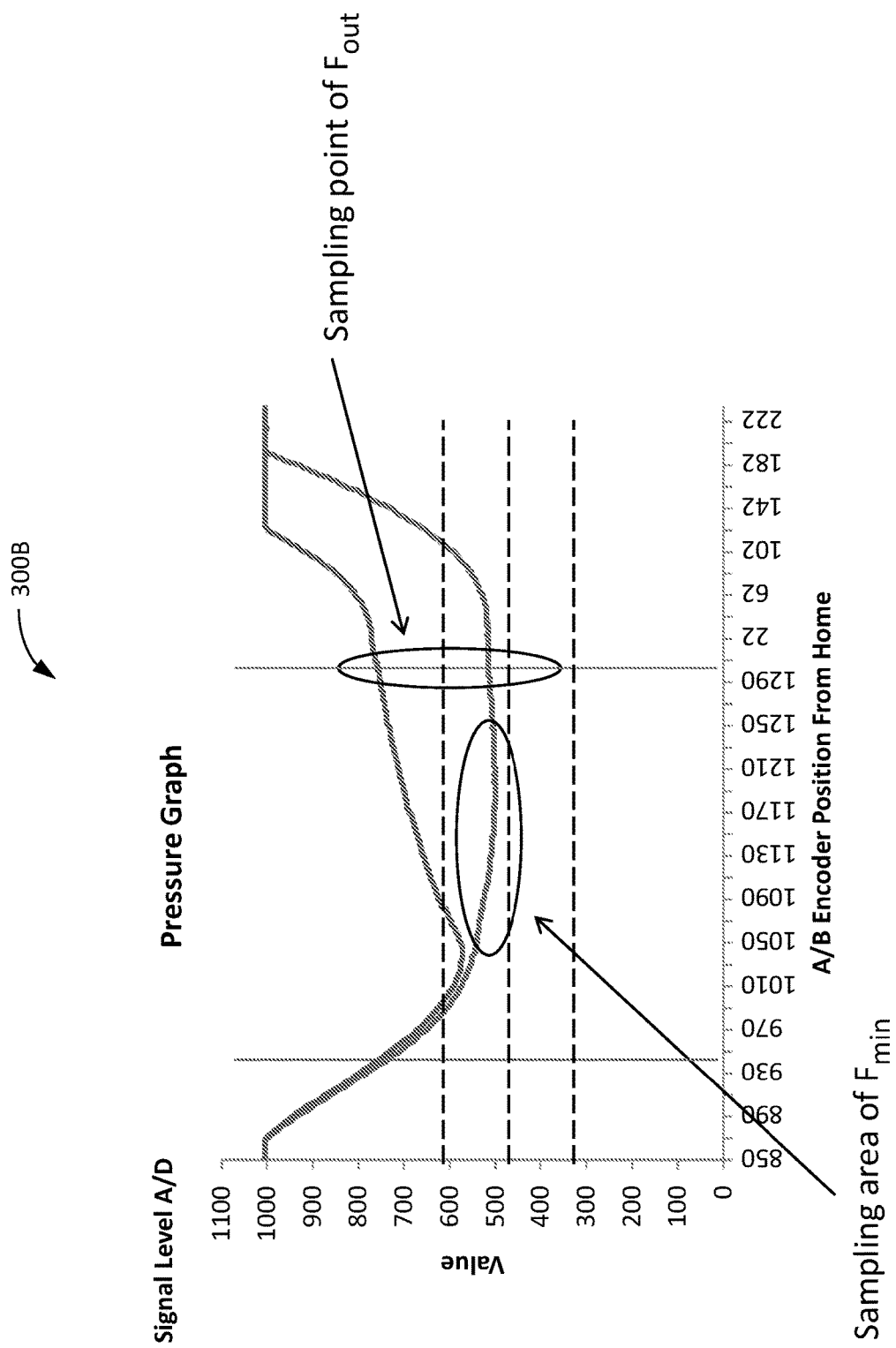

According to a second group of embodiments, the fluid parameter may be an actual output flow rate in which case, controller 206 may detect a fluid parameter is below a first fluid-parameter threshold (in this example a flow rate threshold). If the detected flow rate is below the first fluid-parameter threshold, controller 206 may cause medical device 202 to stop a therapeutic action/functionality such as pumping. Optionally, after a predetermined stall/waiting period controller 206 may analyze the signal from sensor 204 to detect if (a) the fluid parameter has risen above a defined percentage and/or value of the initial/prior parameter, in which case a catheter or occlusion may be indicated and may be differentiated (between occlusion and catheter types) according to the level/value itself or (b) has not risen above the fluid-parameter threshold in which case a non-catheter state may be indicated. Turning to FIG. 3B depicted is graph 300B, associated with the first group of embodiments. Graph 300B shows a output/pressure graph if neither an occlusion nor a catheter is present (bottom line) and a pressure graph showing an occlusion or catheter (top line), signal analysis of the signal at the sampling point (see vertical lines) compared to minimal value for that graph may be carried out. Optionally, a catheter may be differentiated from an occlusion by analyzing the value of Fout-Fmin (Fout may be defined as the ND value of the sensor output at the sampling point, for example at the beginning of a cycle and may indicate the downstream pressure. Fmin may be the lowest point on the same graph. The difference between Fout-Fmin may also be termed Delta A/D).

Figure 3C:
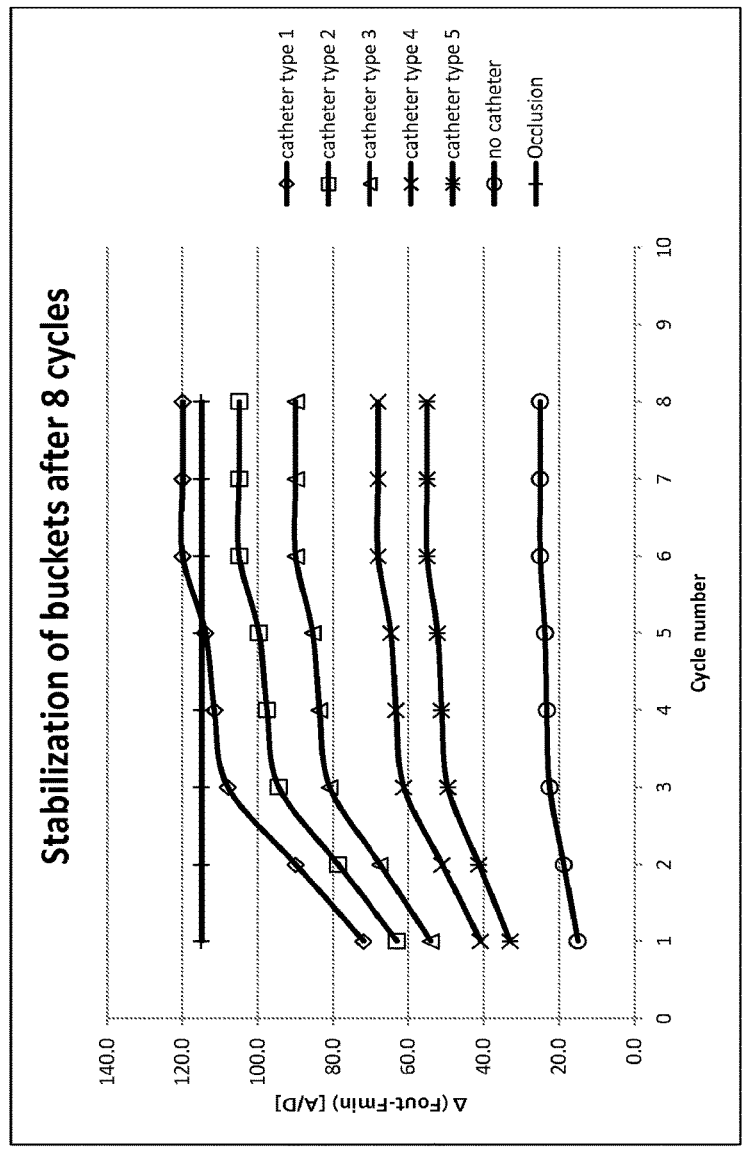

According to a third group of embodiments, controller 206 may, after a predetermined number of cycles (N), compare a fluid parameter to one or more expected parameter ranges, and based on an analysis determine if an occlusion or catheter are detected or if operation of the medical device can proceed/continue without change. If an occlusion is detected, controller 206 may cause medical device 202 to stop a therapeutic action/functionality such as pumping. The fluid parameter may be fluid pressure, fluid flow rate or otherwise and the fluid-parameter threshold may be a pressure threshold and/or a flow rate or otherwise. Optionally, the predetermined number of cycles may be at the beginning/ramp-up/initiation segment of a therapeutic round but could also take place in the middle of the therapeutic round or otherwise. Turning to FIG. 3C, shown is graph 300C including example sensor output for several example catheters and for an occlusion. In this example the signal is analyzed after 8 pumping cycles, however it is understood any N number of cycles may be selected. The medical device may analyze the sensor output to determine which range the current catheter belongs to, based on a similar analysis. (I.e. a catheter with results after 8 cycles near and below 60 may be considered a type 5 catheter). It is understood that if a catheter exceed the maximal catheter range (such as catheter type 1 in example graph 300C), it may be considered by the medical device a de facto occlusion and trigger an occlusion alarm and may further be handled as an occlusion.

Generally and in accordance with all the example groups of embodiments discussed above, controller 206 may carry out signal analysis to compare an expected sensor signal behavior compared to a received signal behavior to detect either an occlusion or catheter 212. Controller 206 may analyze signal parameters such as: signal ramp-up rate, signal change rate, signal behavior (exponential, linear or otherwise), signal plateau level, signal result (such as above/below threshold at determined time).

According to some embodiments, a user may input a catheter indication, which may include additional information such as catheter parameters. The user may input the catheter indication via I/O 214 and/or display 216 (which may be a touch screen). Controller 206 may optionally verify/confirm existence of the catheter as indicated by the user for example by the embodiments discussed above.

According to some embodiments, and compliant with all three groups of embodiments described above, hysteresis operator 217 may modify a catheter bucket threshold based on the detected catheter bucket, if a catheter is indicated. Accordingly, in order to reach a catheter bucket a first bucket threshold needs to be surpassed, however, in order to transition back down to a lower bucket a second bucket threshold needs to be passed. The second bucket threshold may be substantially lower than the first bucket threshold. Hysteresis operator 217 may enable the medical device to avoid switching back and forth between two bucket groups if the catheter causes an increase in backpressure or reduction in flow rate that is near the first bucket threshold. Furthermore, a hysteresis operator may increase the medical device sensor resilience to noise.

According to some embodiments, if an occlusion is detected, controller 206 may cause an alarm to be emitted via alarm device 218.

According to some embodiments, if a catheter is detected, controller 206 may cause detected catheter parameters and information to be displayed on display 216 or output to a remote computer/server via transceiver 220.

According to some embodiments, if a catheter is detected, controller 206 may relay feedback, optionally via feedback circuit 222 in controller 206, causing the first fluid-parameter threshold to be updated so that unneeded occlusion alarms are not triggered (for example stemming from the detected catheter 212 and not an occlusion).

According to some embodiments, if a catheter is detected, controller 206 may optionally utilize feedback circuit 22 to cause the flow rate to be updated so that a nominal/requested flow rate is achieved taking into account the effect of the catheter's backpressure and additional parameters such as catheter parameters and more. Optionally, a confirmation may be requested from the user in order to correct the flow rate.

According to some embodiments, if catheter 212 is detected, controller 206 may cause a notification to be displayed recommending an updated flow rate to the user. Optionally, the controller may relay the message via display 216. For example, a message may be displayed if the catheter diameter is below a minimal width or if the flow rate is different than the requested/nominal flow rate because of existence of the catheter.

According to some embodiments, parameters associated with the flow rate such as speed/velocity of medical device 202 motor, cycle rate or otherwise may be corrected/updated so that a nominal/requested flow rate may be achieved. The parameters associated with flow rate may be updated by controller 206 (optionally via feedback 222) based on: (a) detected catheter parameters such as catheter group/type and or catheter: width, diameter, length, compliance, downstream location/distance and more, (b) user indicated/requested flow rate and/or (c) additional system information such as existence of blockage in the vein or otherwise.

According to some embodiments, after detection of existence of catheter 212, controller 206 may carry out steps to detect the catheter type/group/bucket or these may be indicated according to the signal analysis. In accordance with the first group of embodiments discussed above, for example, if the catheter is detected when a pressure is detected by sensor 204 as having passed or exceeding the fluid-parameter threshold, the threshold may be increased and these steps (checking pressure and increasing threshold) may be carried out again until the catheter does not cause backpressure above the modified threshold.

According to some embodiments, if a detected catheter exceeds the maximal catheter group/bucket optionally, (for example for clinical or medical reasons or otherwise) then controller 206, optionally, may emit a notification on display 216 indicating that the nominal flow rate cannot be achieved or recommending the user consider changing the requested flow rate.

According to some embodiments, catheter 212 may belong to one or more groups of catheters or buckets of catheters. The groups may be differentiated based on, for example: diameter range, length range, compliance range, flow rate with given catheter and/or otherwise, so that a catheter group/bucket has similar characteristics for example in causing similar backpressure when operating in conjunction with medical device 202 and downstream from conduit 208. Conduit 208 may have a fixed or known characteristic(s) or be one out of a group of possible conduits so that the catheter group/buckets may also be dependent on the conduit's characteristics/parameter (such as diameter, length, compliance etc.).

According to some embodiments, conduit 208 may be utilized to transfer fluids which may include some gases. Some examples of fluid include: water, saline, medicine, TPN, blood, a combination of these and more.

According to some embodiments, conduit 208 may be connected downstream from the medical device, to a patient. The connection to the patient may be intravascular, intra-arterial, parenteral, subcutaneous, intravenous, epidural, enteral, perineural and intrathecal routes and more. As discussed the connection to a patient, may include catheter 212 or not.

According to some embodiments, catheter 212 may be any conduit more narrow than conduit 208 and may cause an increase in backpressure and/or a change in the actual flow rate (so that the actual flow rate is different than the nominal or requested flow rate) from the catheter toward the medical device. Some types of catheters may include: epidural catheter, peripherally inserted central catheter (PICC), umbilical catheter, spinal needle, pediatric catheter and more.

Turning to FIG. 4, shown is a flow chart (400) of an example method in accordance with some embodiments. It is understood that the steps may be carried out in conjunction with some of the elements discussed with regard to FIGS. 1 and 2.

According to some embodiments, while a medical device is operating and optionally, during an initial phase, or a start-up phase, a signal indicative of fluid condition/parameters may be received (step 402). Some examples of fluid parameters (which may also be termed parameters associated with the fluid) may include: fluid flow rate, occlusion of fluid, air bubble detection, fluid/conduit pressure and more. Optionally, the signal received at step 402 may also include a user indication that a catheter is expected downstream.

According to some embodiments the medical device may carry out signal analysis (step 404) to detect/monitor if a catheter is indicated (step 406) based on the received signal. Some examples of signal analysis may include detecting when the received signal passes or exceeds a threshold, behavior of the signal indicates a catheter and/or a value of the signal compared to a range of values at a predetermined point, time or cycle and/or a look-up table for a value of the signal or otherwise.

According to some embodiments, if a catheter is not detected the medical device may continue monitoring the received signal for an occlusion and/or for a catheter.

If a catheter is indicated then further analysis to detect the type/bucket or group of the catheter may be carried out (step 408). It is understood that depending on the signal analysis type, step 408 may at least partially be carried out in conjunction with step 404 or 406 (So that the catheter is both indicated and it's type/group/bucket identified at substantially the same time during the same analysis). Furthermore, it is understood that if a catheter exceeds the maximal catheter bucket/group then it may either be detected as an occlusion or the catheter may be considered by the medical device to be an occlusion as the medical device may not be able to compensate for such a catheter due to, for example, extremely high backpressure or the medical device may monitor for an occlusion (step 407).

According to some embodiments, optionally, a flow rate or parameters associated with the flow rate may be updated based on the detected catheter type/group (step 410). Optionally, thresholds may be updated (step 412). For example, a pressure threshold may be updated so that backpressure stemming from the catheter (and not an occlusion) does not trigger an occlusion alarm; or a bucket threshold may be updated in accordance with a hysteresis operator. Optional step 412 may also be carried out in conjunction to detecting the catheter type as will become evident in further discussions of additional methods to follow.

According to some embodiments, after a catheter is detected the medical device may monitor for either a change in catheter bucket and/or an occlusion (step 414).

Figure 5A:
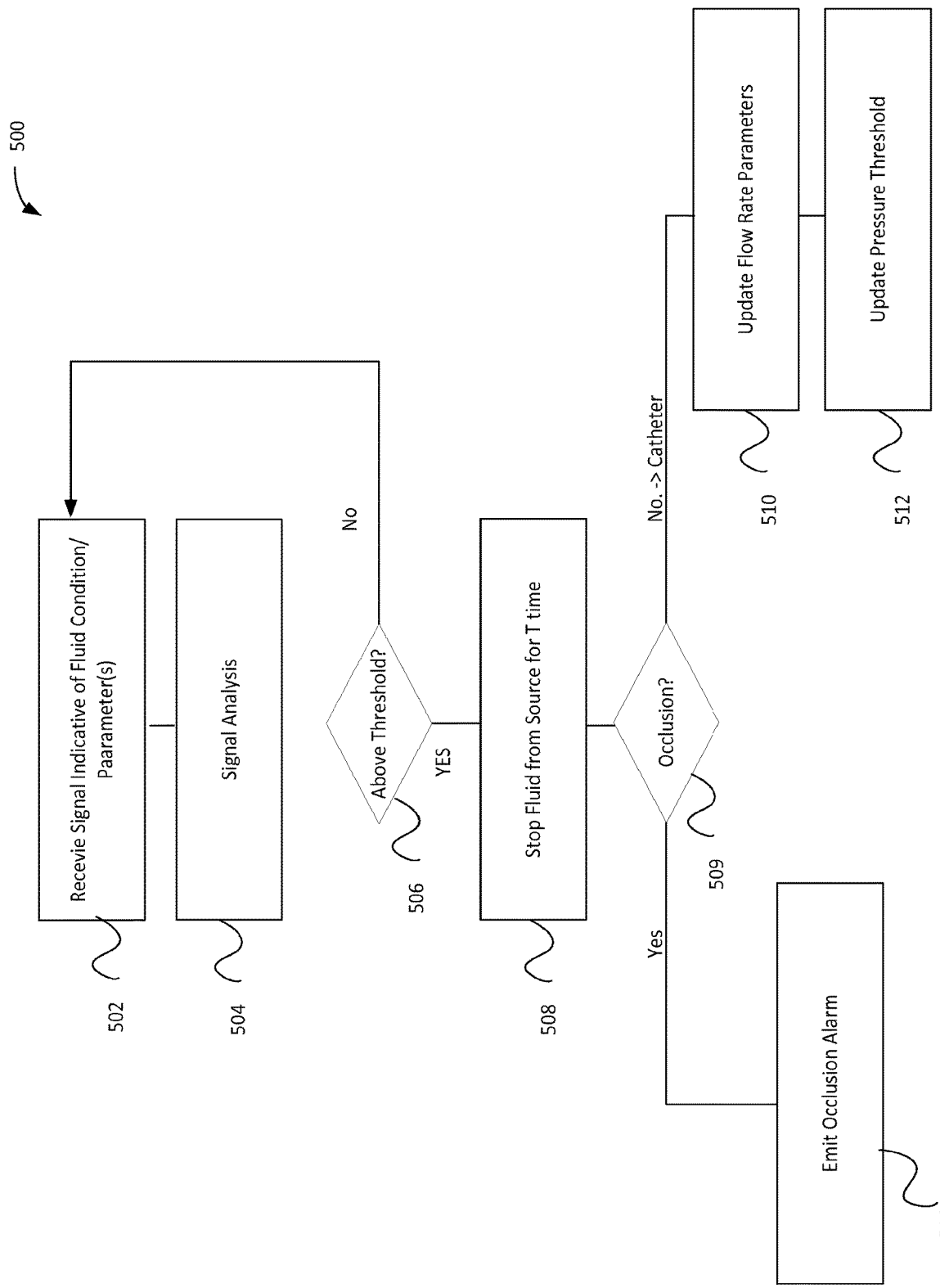
FIGS. 5A and 5B are flow charts of example methods in accordance with some embodiments of the present invention.

Turning to FIG. 5A, shown is a flow chart (500) of an example method in accordance with some embodiments. It is understood that the steps may be carried out in conjunction with some of the elements discussed with regard to FIGS. 1 and 2. Furthermore elements 502, 504, 510 and 512 are substantially similar to elements 402, 404, 410 and 412 appropriately. If the received signal and/or the signal analysis detect that the pressure is above a threshold (step 506) then the medical device may stop pumping of the fluid from the source for a predetermined length of time (T) (step 508). The length of time T (or a sampling point) may be determined according to typical signal characteristics and may be several seconds or otherwise. A signal analysis of the received signal after the temporary halt/stop time (T) may differentiate between a pressure above the threshold that stems from an occlusion and one that stems from a catheter or otherwise (step 509). If an occlusion is detected than an occlusion alarm may be emitted (step 514).

Figure 5B:
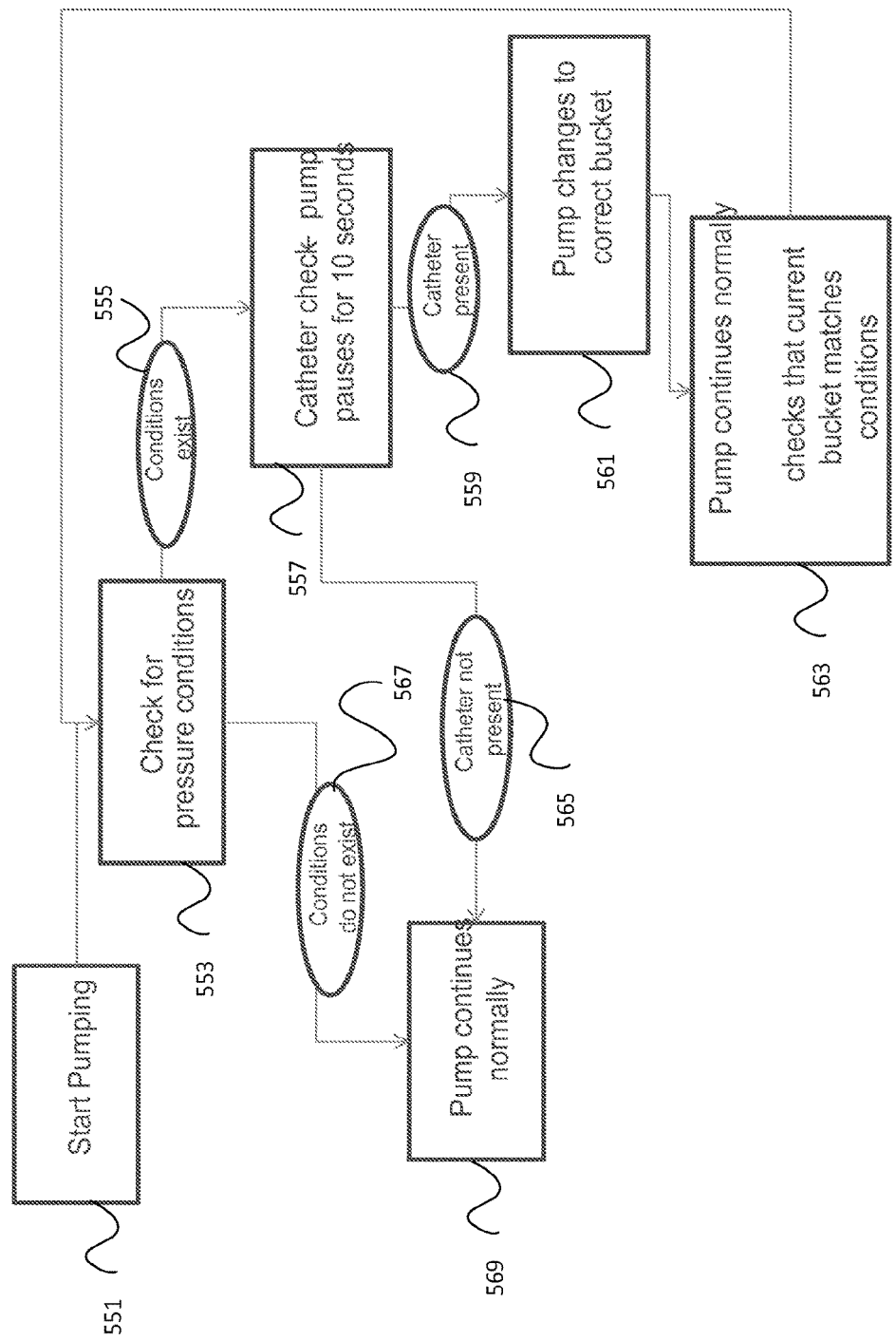

Turning to FIG. 5B, shown is a flow chart (550) of an example method in accordance with some embodiments. A medical pump may start/initiate a pumping action (step 551), a micro-controller of the medical device may check for pressure conditions based on a signal received from a sensor of the medical device (step 553). If the condition exists (step 555), then a catheter-check may be carried out including stopping the pumping action for approximately 10 seconds (step 557). If a catheter is detected/analyzed to be present (step 559) based on signal analysis of the sensor signal following stopping of the pumping action, then a catheter bucket may be updated (step 561) a catheter bucket may also cause a pressure condition threshold or parameter to be updated. The pump may continuously or periodically check during the pumping process that the current bucket matches conditions (step 563) and that, for example the nominal flow rate is substantially met and that unneeded occlusion alarms (stemming from the catheter and not a real occlusion) are not detected. If a catheter is not present (step 565) or a pressure condition is not detected (step 567) the pump may continue its normal operation (step 569).

Figure 6A:
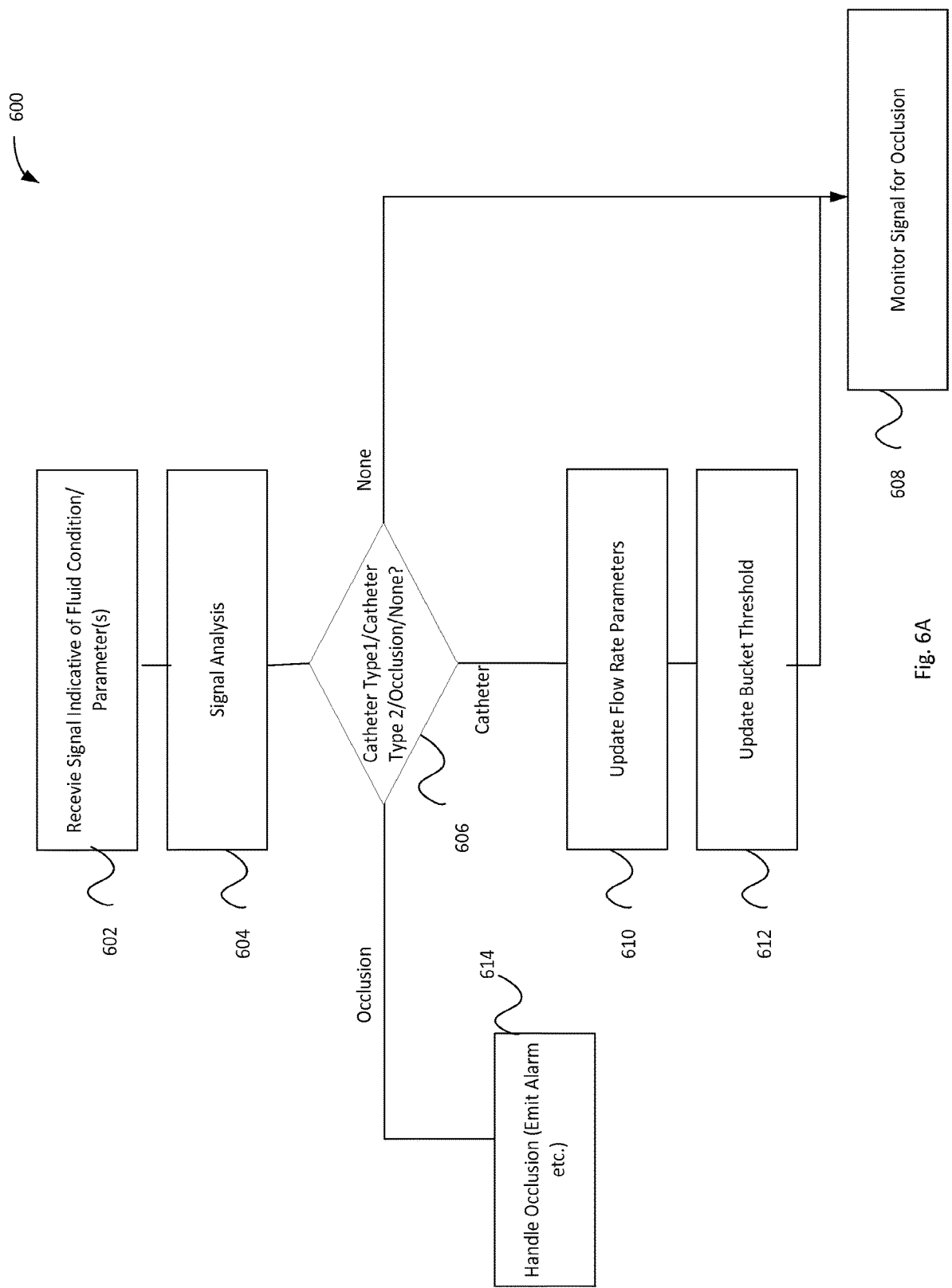
FIGS. 6A and 6B are flow charts of example methods in accordance with some embodiments of the present invention.

Turning to FIG. 6A, shown is a flow chart (600) of an example method in accordance with some embodiments. It is understood that the steps may be carried out in conjunction with some of the elements and example embodiments discussed with regard to FIGS. 1 and 2.

According to some embodiments, while a medical device is operating and optionally, during an initial phase, or a start-up phase, a signal indicative of fluid condition/parameters may be received (step 602). Some examples of fluid parameters may include: fluid flow rate, occlusion of fluid, air bubble detection, fluid/conduit pressure. Optionally, the signal received at step 602 may also include a user indication that a catheter is expected downstream.

According to some embodiments the medical device may carry out signal analysis (step 604) to detect/monitor if a catheter, occlusion, or neither is indicated including detecting the group/bucket to which the catheter belongs (step 606) based on the received signal. Some examples of signal analysis may include detecting a signal level/value at a known time or after a determined number of cycles and analyzing to which range the signal belongs. A signal value may indicate a non-catheter condition/indication, for example a signal value within a first range may indicate a neither catheter nor an occlusion, a second or more range may indicate an appropriate catheter group/bucket and a third range may indicate an occlusion. It is understood that a range may include one value/threshold that the signal values may be above or below and/or may include two values/thresholds that the signal value is between.

According to some embodiments, if neither an occlusion nor a catheter is detected the medical device may continue monitoring the received signal for an occlusion (608). If a catheter and the catheter type/bucket are indicated, optionally, a flow rate or parameters associated with the flow rate may be updated based on the detected catheter type/group (step 610). Furthermore, optionally, a catheter bucket threshold may be updated so that a hysteresis function is activated/operable (step 612). If an occlusion is detected then the occlusion may be handled as defined by the medical device (step 614).

Figure 6B:
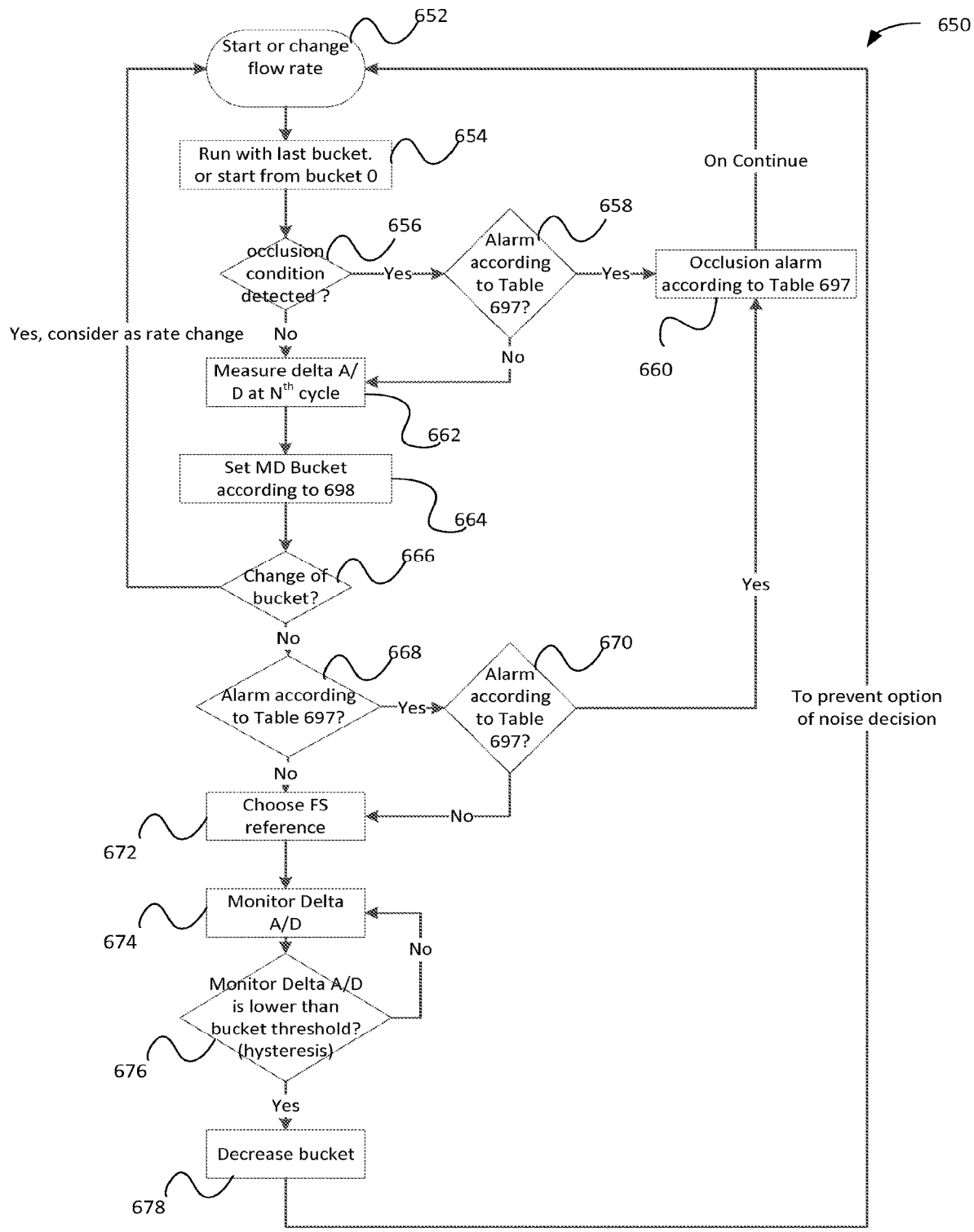

Turning to FIG. 6B, shown is a flow chart (650) of an example method in accordance with some embodiments. It is understood that the steps may be carried out in conjunction with some of the elements and example embodiments discussed with regard to FIGS. 1 and 2.

According to some embodiments, a flow rate may be started or changed by a user (step 652), as a default the method may start with a previously detected catheter bucket (during the current therapeutic round which may include a few or many cycles) and if no previous bucket was detected the lowest bucket may be the default (step 654). During the first N cycles the medical device may monitor for an occlusion triggering state (step 656). If an occlusion is detected, table 697 (of FIG. 6C) may be referred to (step 658), generally if an upstream occlusion is detected an occlusion alarm may be triggered (step 660) regardless of if N cycles have been reached, and if a downstream occlusion is suspected the medical device may complete N cycles before analyzing the occlusion. After N cycles the sensor output may be analyzed (for example, the delta A/D value) (step 662), based on the analyzed signal the medical device (MD) may be set to the default catheter bucket according to table 698 of FIG. 6D (step 664) and the detected catheter bucket may be stored as the default catheter bucket for the current medical device administration/therapeutic round (see step 654). The medical device may compare the detected catheter bucket to the previous/expected catheter bucket (step 666) and if catheter bucket is modified may re-run the initiation/start-up steps starting from step 652. If the bucket is unchanged the medical device may analyze if an occlusion should be emitted according to table 697 (step 668). If an occlusion alarm is warranted (step 670) an occlusion may be emitted (step 660). If an occlusion is not detected the start-up sequence may be concluded, in which case the sensor output may be analyzed in a different manner than in the start-up sequence (step 672), for example, until the sensor output is considered stabilized the medical device may analyze the delta A/D value and after it is considered stable; a reference signal may be selected/detected after which the medical device may analyze the Force output instead (Fout) (step 674). The medical device may still substantially continuously monitor the Delta A/D to detect if the sensor output is below a bucket threshold (step 676) and may need to switch to a lower catheter bucket (step 678). If a catheter bucket is decreased the medical device may re-initiate the start-up sequence (Step 652). It is understood that a hysteresis operation may be applied to the catheter bucket threshold (see table 699 of FIG. 6E), so that the bucket is detected according to a first bucket threshold (see step 664 and table 698) but the bucket threshold in order to transition to a lower bucket (See step 676 and table 699) is lower than the first bucket threshold. Accordingly, in order to transition to a second bucket a higher bucket threshold needs to be surpassed but in order to transition from the second bucket back down to a lower first bucket a lower threshold need to be passed so that noise and calculation accuracy do not cause the medical device to transition back and forth between two catheter buckets. According to some embodiments N cycles may be, for example, any number of cycles between 1-30 or otherwise including a part of a cycle.

N may be predetermined so that the sensor signal is stabilized and the medical device is in a substantially steady state before analyzing to detect an occlusion.

Turning to FIG. 7A, shown is a chart of (700A) an example summary/comparison table in accordance with some embodiments including example values. The left column shows different types of example catheters. The next two columns show the accuracy for two different requested flow rates (if catheter detection were not carried out). The "bucket" column shows the group that the catheter would be classified to. The next column shows the conversion factor for the flow rate according to bucket and the next column shows the threshold value for most medical devices and the final column shows the threshold value for epidural pumps or modes (which start at a higher bucket value because a catheter is typically present when infusing to the epidural space Turning to FIG. 7B, shown is a chart with example results in accordance with some embodiments. The first column indicates the catheter type/bucket. The second column may indicate the deviation if a flow rate parameter is not corrected/compensated for. The third column may indicate the bucket type. The fourth column may indicate the percentage of change to flow parameter and the fifth column indicates the corrected accuracy.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

The invention claimed is:

1. A medical device for delivering fluid to a patient, said device comprising:
   a pump including a pumping mechanism designed to pump fluid through a conduit;
   a pressure sensor positioned to sense pressure within the conduit and to generate signals in response thereto; and
   a controller communicatively coupled to said sensor and said pump, said controller comprising processing circuitry configured to dynamically modify and update velocity or cycles of said pumping mechanism, during operation of said pumping mechanism, based on said signals from said pressure sensor, so as to maintain a desired flow rate within the conduit,
   wherein said controller is configured to:
   (i) analyze said signals to determine if the pressure within the conduit is indicative of a backpressure within the conduit passing above a backpressure-threshold;
   (ii) in response to determining in step (i) that the backpressure within the conduit is above the backpressure-threshold, determine the presence of a catheter having an internal diameter that is narrower than the internal diameter of the conduit coupled to the conduit downstream of the pump, and adjust the velocity or cycles of the pumping mechanism based on the backpressure within the conduit being above the backpressure-threshold;
   (iii) in response to determining in step (i) that the backpressure within the conduit is not above the backpressure-threshold, determine the non-presence of a catheter having an internal diameter that is narrower than the internal diameter of the conduit coupled to the conduit downstream of the pump;
   (iv) in response to determining the non-presence of a catheter based on the analyzing of said signals, continue operation of the pump, and when said signals indicate that pressure sensed by said pressure sensor is over an occlusion-threshold, issue an alarm indicative of an occlusion within the conduit; and
   (v) in response to determining the presence of a catheter having an internal diameter that is narrower than the internal diameter of the conduit based on the backpressure within the conduit being above the backpressure-threshold, increase a value of the occlusion-threshold.

2. The device of claim 1, wherein said controller is configured to update velocity or cycles of said pumping mechanism, during operation of said pumping mechanism, based on periodic signals from said pressure sensor, sampled by said pressure sensor after a defined number of cycles, a defined number of cam rotations or a defined length of time.

3. The device of claim 1, wherein, in response to determining the presence of a catheter, said controller is further configured to determine a catheter flow group characterization of a catheter coupled to the conduit downstream of the pump, based on the signals from said pressure sensor.

4. The device according to claim 3, further comprising a hysteresis operator configured to prevent transition between catheter flow group characterization determinations due to noise.

5. The apparatus according to claim 4, wherein the hysteresis operator is configured to prevent transition between catheter flow group characterization determinations by, in response to determining a catheter flow group characterization of the catheter, changing a backpressure-threshold corresponding to the catheter flow group characterization so as to inhibit the controller from transitioning to a different catheter flow group characterization determination due to noise.

6. A method for operating a medical device for delivering fluid to a patient, said method comprising:
   using a pressure sensor to sense pressure within a fluid conduit delivering fluid to the patient and generate signals in response thereto; and
   using a controller:
   (i) analyzing said signals to determine if the pressure within the conduit is indicative of a backpressure within the conduit passing above a backpressure-threshold;
   (ii) in response to determining in step (i) that the backpressure within the conduit is above the backpressure-threshold, determining the presence of a catheter having an internal diameter that is narrower than the internal diameter of the conduit coupled to the conduit downstream of the pump, and adjusting the velocity or cycles of the pumping mechanism based on the backpressure within the conduit being above the backpressure-threshold;
   (iii) in response to determining in step (i) that the backpressure within the conduit is not above the backpressure-threshold, determining the non-presence of a catheter having an internal diameter that is narrower than the internal diameter of the conduit coupled to the conduit downstream of the pump;
   (iv) dynamically modifying and updating velocity or cycles of a pumping mechanism of a pump causing the fluid to flow through the conduit, during operation of said pump, based on said signals from said pressure sensor, so as to maintain a desired flow rate within the conduit;

(v) in response to determining the non-presence of a catheter based on the analyzing of said signals, continuing to operate the pump, and when said signals indicate that pressure sensed by said pressure sensor is over an occlusion-threshold issuing an alarm indicative of an occlusion within the conduit; and (vi) in response to determining the presence of a catheter having an internal diameter that is narrower than the internal diameter of the conduit based on the backpressure within the conduit being above the backpressure-threshold, increasing a value of the occlusion-threshold.

7. The method of claim 6, wherein further comprising updating velocity or cycles of said pumping mechanism, during operation of said pumping mechanism, based on periodic signals from said pressure sensor, sampled by said pressure sensor after a defined number of cycles, a defined number of cam rotations or a defined length of time.

8. The method of claim 6, further comprising, in response to determining the presence of a catheter, determining a catheter flow group characterization of a catheter coupled to the conduit downstream of the pump based on the signals from said pressure sensor.

9. The method of claim 8, further comprising applying a hysteresis operation to prevent transition between catheter flow group characterization determinations due to noise.

10. The method according to claim 9, wherein applying the hysteresis operation comprises, in response to determining a catheter flow group characterization of the catheter, changing a backpressure-threshold corresponding to the catheter flow group characterization so as to inhibit the controller from transitioning to a different catheter flow group characterization determination due to noise.

\* \* \* \* \*